United States Patent
Qian et al.

(10) Patent No.: US 9,562,225 B2
(45) Date of Patent: Feb. 7, 2017

(54) INTERNALIZATION OF PROTEINS INTO HOLLOWED GOLD NANOSTRUCTURES

(71) Applicants: Xi Qian, Troy, NY (US); Jennifer E. Gagner, Boston, MA (US); Jonathan S. Dordick, Schenectady, NY (US); Richard W. Siegel, Menands, NY (US)

(72) Inventors: Xi Qian, Troy, NY (US); Jennifer E. Gagner, Boston, MA (US); Jonathan S. Dordick, Schenectady, NY (US); Richard W. Siegel, Menands, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 0 days.

(21) Appl. No.: 14/676,258

(22) Filed: Apr. 1, 2015

(65) Prior Publication Data
US 2016/0097081 A1    Apr. 7, 2016

Related U.S. Application Data

(60) Provisional application No. 62/106,390, filed on Jan. 22, 2015, provisional application No. 62/060,776, filed on Oct. 7, 2014.

(51) Int. Cl.
| | |
|---|---|
| *C12N 11/14* | (2006.01) |
| *C12N 9/36* | (2006.01) |
| *C23C 18/16* | (2006.01) |
| *B82Y 40/00* | (2011.01) |
| *C23C 18/54* | (2006.01) |
| *A61K 47/48* | (2006.01) |

(52) U.S. Cl.
CPC ......... *C12N 11/14* (2013.01); *A61K 47/48861* (2013.01); *A61K 47/48884* (2013.01); *B82Y 40/00* (2013.01); *C12N 9/2462* (2013.01); *C12Y 302/01017* (2013.01); *C12Y 304/21001* (2013.01); *C23C 18/1635* (2013.01); *C23C 18/1657* (2013.01); *C23C 18/54* (2013.01)

(58) Field of Classification Search
None
See application file for complete search history.

(56) References Cited

PUBLICATIONS

Xia et al., Accounts of Chemical Research, Gold Nanocages: From Synthesis to Theranostic Applications, Apr. 29, 2011, pp. 914-924, vol. 44, No. 10.
Yavuz et al., Gold Nanocages Covered by Smart Polymers for Controlled Release With Near-Infrared Light, Nature Materials, 8:935-939, Nov. 1, 2009.
Sun et al., JACS Articles, Mechanistic Study on the Replacement Reaction Between Silver Nanostructures and Chlorauric Acid in Aqueous Medium, Mar. 3, 2004, pp. 3892-3901, vol. 126, No. 12.
Takahashi et al., Nano Letters, Three-Dimensional Electron Density Mapping of Shape-Controlled Nanoparticle by Focused Hard X-ray Diffraction Microscopy, Apr. 19, 2010, pp. 1922-1926.
Hu et al., J. Phys. Chem, Correlated Rayleigh Scattering Spectroscopy and Scanning Electron Microscopy Studies of Au—Ag Bimetallic Nanoboxes and Nanocages, Jul. 31, 2007, pp. 12558-12565.
Chen et al., Advanced Functional Materials, Gold Nanocages: A Novel Class of Multifunctional Nanomaterials for Theranostic Applications, Oct. 4, 2010, pp. 3684-3694.
Gagner et al., Biomaterials 33:8503-8516, Effect of Gold Nanoparticle Structure on the Conformation and Function of Adsorbed Proteins, Aug. 17, 2012.
Skrabalak, et al., Accounts of Chemical Research, 41:1587-1595, Gold Nanocages: Synthesis, Properties, and Applications, Jun. 21, 2008.
Shi et al., Adv. Funct. Mat., 24:826-834, Near-Infrared Light-Encoded Orthogonally Triggered and Logical Intracellular Release Using Gold Nanocage@Smart Polymer Shell, Sep. 3, 2013.
Sun et al., Nano Letters, 11:4386-4392, Monitoring of Galvanic Replacement Reaction Between Silver Nanowires and HAuCl4 by In Situ Transmission X-ray Microscopy, Sep. 6, 2011.
Vertegel et al., Silica Nanoparticle Size Influences the Structure and Enzymatic Activity of Adsorbed Lysozyme, May 27, 2004, Langmuir, 20:6800-6807.
Rodrigues et al., Chem. Soc. Rev., Modifying Enzyme Activity and Selectivity by Immobilization, Oct. 11, 2012, 42:6290-6307.
Biswas et al, J. Phys. Chem B., Spectroscopic Studies of Catanoionic Reverse Microemulsion: Correlation with the Superactivity of Horseradish Peroxidase Enzyme in a Restricted Environment, May 6, 2008, 112:6620-6628.
Skrabalak et al., Nature Protocols, Facile Synthesis of Ag Nanocubes and Au Nanocages, Sep. 6, 2007, 2:2182-2190.
Qian et al., Cage-Like Nanostructure and its Nano-Bio Interactions with Proteins Confined Inside, 2011 Rensselaer Nanotechnology Center Research Symposium, Oct. 13, 2011, p. 1-19.
Qian et al., Nano-bio Interactions at Concave and Confined Interfaces, 2011 Materials Research Society Fall Meeting, Nov. 26, 2011, p. 1.

(Continued)

*Primary Examiner* — Anand Desai
(74) *Attorney, Agent, or Firm* — Teige P. Sheehan; Heslin Rothenberg Farley & Mesiti P.C.

(57) ABSTRACT

Provided is a gold nanocage with pores, charged ligand molecules covalently bound to internal surfaces of the gold nanocage, and payload molecules electrostatically adsorbed onto said charged ligand molecules, wherein a pore diameter is between 1.2 and 20 times a gyration radius of the payload molecule. Also provided is a method for making a nanoparticle, including using polyvinylpyrrolidone as a capping agent in a galvanic replacement reaction to convert a silver nanocube into a gold nanocage having pores, replacing the polyvinylpyrrolidone on internal surfaces with charged ligand molecules, and electrostatically adsorbing payload molecules onto the charged ligand molecules, with a pore diameter less than twenty times a gyration radius of the payload molecule. Also provided is a method of delivering a pharmacological agent to a mammalian cell, including contacting the cell with a gold nanocage having pores, ligand molecules bound to internal surfaces, and pharmacological agent adsorbed onto ligand molecules.

21 Claims, 5 Drawing Sheets

(56) References Cited

PUBLICATIONS

Qian et al., Using Gold Nanocage to Study the Effects of Concave and Confined Surfaces on Immobilized Proteins, Department of Material Science and Engineering, Rensselaer Polytechnic Institute, Oct. 29, 2014, 2014 Rensselaer Nanotechnology Center Research Symposium, 16 pages.

Qian et al., Langmuir, Protein Immobilization in Hollow Nanostructures and Investigation of the Adsorbed Protein Behavior, Jan. 22, 2014, 30:1295-1303.

Wang et al., A Comparison Study of Gold Nanohexapods, Nanorods, and Nanocages for Photothermal Cancer Treatment, ACS Nano, Mar. 26, 2013, 7:2068-2077.

Larsericsdotter et al., Thermodynamic Analysis of Proteins Adsorbed on Silica Particles: Electrostatic Effects, Journal of Colloid and Interface Science, May 1, 2001, pp. 98-103.

INTERNALIZATION OF PROTEINS INTO HOLLOWED GOLD NANOSTRUCTURES

CROSS-REFERENCE TO RELATED APPLICATIONS

This application claims priority under 35 U.S.C. §119 to U.S. Provisional Application No. 62/106,390, filed Jan. 22, 2015, which is herein incorporated by reference in its entirety, and 62/060,766, filed Oct. 7, 2014, which is herein incorporated by reference in its entirety.

GOVERNMENT RIGHTS STATEMENT

This invention was made with U.S. Government support under NSF-NSEC-DMR-0642573 awarded by the National Science Foundation. The U.S. Government has certain rights in the invention.

BACKGROUND OF THE INVENTION

Technical Field

The present invention generally relates to use of hollow nanoparticles as carriers of biomolecules, therapeutic agents, and other molecular compounds of interest. More particularly, the present invention relates to hollow gold nanocages carrying molecular targets electrostatically adsorbed onto their interior surfaces.

Background Information

Hollow gold nanoparticles, also known as gold nanocages, are effective vehicles for the transport and administration of therapeutic agents, bioactive compounds, biomolecular reagents, biocatalysts, and other molecular compounds of interest. However, better control of the bioavailability of gold nanocages' content is needed. It is therefore desirable to obtain gold nanocages whose profile of packaging and release of carried molecules can be better controlled.

SUMMARY OF THE INVENTION

The shortcomings of the prior art are overcome, and additional advantages are provided, through the provision, in one aspect, of a nanoparticle. The nanoparticle includes a gold nanocage with pores, charged ligand molecules covalently bound to one or more surfaces of the gold nanocage wherein at least some charged ligand molecules are covalently bound to internal surfaces of the gold nanocage, and payload molecules electrostatically adsorbed onto said charged ligand molecules covalently bound to internal surfaces of the gold nanocage, wherein a diameter of one or more pores in the gold nanocage is between 1.2 and 20 times a gyration radius of the payload molecule.

A method of making a nanoparticle is also provided. The method includes using a galvanic replacement reaction to convert a silver nanocube into a gold nanocage with pores wherein a capping agent comprises polyvinylpyrrolidone, removing polyvinylpyrrolidone molecules from the gold nanocage and replacing the polyvinylpyrrolidone molecules with charged ligand molecules wherein replacing comprises covalently binding charged ligand molecules to internal surfaces of the nanocage, electrostatically adsorbing payload molecules onto charged ligand molecules that are covalently bound to internal surfaces of the nanocage.

A method of delivering a pharmacological agent to a mammalian cell is also provided. The method includes contacting the cell with a gold nanocage having pores, wherein charged ligand molecules are covalently bound to one or more surfaces of the gold nanocage and molecules of the pharmacological agent are electrostatically adsorbed onto charged ligand molecules that are covalently bound to internal surfaces of the nanocage.

Additional features and advantages are realized through the techniques of the present invention. These and other objects, features and advantages of this invention will become apparent from the following detailed description of the various aspects of the invention taken in conjunction with the accompanying drawings.

BRIEF DESCRIPTION OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

DETAILED DESCRIPTION OF THE INVENTION

Aspects of the present invention and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific examples, while indicating embodiments of the invention, are given by way of illustration only, and are not by way of limitation. Various substitutions, modifications, additions and/or arrangements within the spirit and/or scope of the underlying inventive concepts will be apparent to those skilled in the art from this disclosure.

The present disclosure provides, in part, nanoparticles for the transport and administration of therapeutic agents, bioactive compounds, biomolecular reagents, biocatalysts, and other molecular compounds of interest, referred to generally herein as payload molecules (e.g., nucleic acids, polypeptides, enzymes, antibodies, or phospholipids). Gold nanocages with such payload molecules electrostatically adsorbed onto their surfaces as disclosed herein possess high biocompatibility and can be designed for controlled duration and bioavailable concentration of payload molecules. For example, gold nanocages with payload molecules electrostatically adsorbed onto their interior surfaces but not substantially onto their external surfaces are particularly advantageous in that desirable, controlled activity of internally adsorbed payload molecules can be maintained while minimizing or eliminating undesirable effects of interactions of payload molecules adsorbed onto external surfaces with other nanocages or with other unintended substrates, preserving the intended controlled functionality of internally adsorbed payload molecules.

Figure 1A:
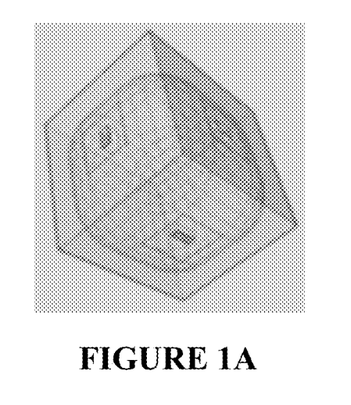
FIGS. 1A-1B are diagrammatic representations of gold nanocages.
Figure 1B:
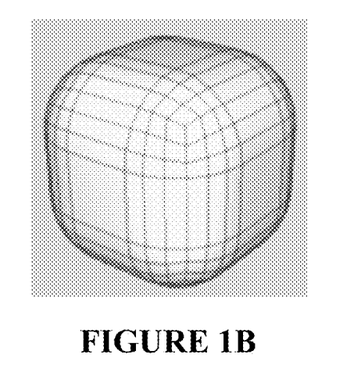
Figure 1C:
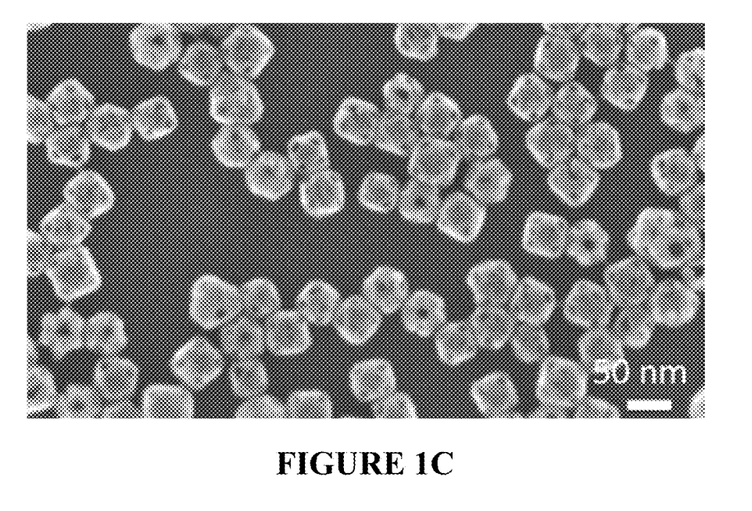
FIG. 1C is a scanning electron micrograph of gold nanocages.

In one aspect, complexes of gold nanocages with payload molecules are formed by adsorbing payload molecules electrostatically onto the surfaces of the gold nanocages. Gold nanocages are substantially cube-shaped nanoparticles. Their edges may be anywhere from between 40 nm and 100 nm in length and they may possess hollow, nearly spherical cores with diameters between 5-50 nm. The walls of gold nanocages, between the internal hollow cores and the external environment, may be approximately 10 nm thick. However, skilled artisans would recognize that gold nanocages with overall sizes, pore sizes, hollow core sizes, and wall thicknesses that differ from the foregoing dimensions may be made by modifying parameters of gold nanocage synthesis. FIG. 1A is a diagrammatic representation of a gold nanocage with the internal hollow core and pores represented by dotted lines. FIG. 1B is a diagrammatic representation of the hollow core of a gold nanocage. FIG. 1C is a scanning electron micrograph of gold nanocages, with a scale bar showing 50 nm.

Gold nanocages may be formed from solid silver nanocubes by a galvanic replacement reaction, resulting in hollow, porous structures consisting of a gold-silver alloy with a ratio of Au:Ag of approximately 3:1. In addition to external surface areas, such nanoparticles also have available surface area lining their hollow interior cores and pores, referred to herein as internal surface area. Solvents and solutes, including payload molecules, can access the hollow interior and internal surface areas through pores that connect the nanoparticles' hollow interiors with the external environment. Charged ligands may be attached, covalently or otherwise, to the surfaces of the gold nanocages, creating charged surface areas on internal and external surfaces. Subsequent incubation of such gold nanocages with payload molecules with a charge opposite that of the charged ligand molecules results in the adsorption of payload molecules onto internal and external surfaces.

In another aspect, payload molecules may be desorbed from surfaces of the gold nanocages. Electrostatic attraction of payload molecules to charged ligand molecules may be disturbed by increasing the concentration of salt in a solution in which the nanocages are held, and/or by modifying the pH of such solution so as to decrease the charge differential between charged ligand and payload molecules, resulting in desorption.

In a further aspect, payload molecules may be readsorbed back onto gold nanocages' surfaces such as by returning the ionic strength or pH to the levels that existed upon initial adsorption. Importantly, given the morphology and size of gold nanocages' hollow interiors and pore dimensions, stimulation of readsorption may result in selective readsorption of payload molecules onto the interior surfaces of the gold nanocages but not onto exterior surfaces. Depending on, for example, the size of the payload molecules, the maximum diameter or width of pores and pores' length, and duration of desorption before readsorption, the local concentration of desorbed payload molecules within the hollow interior of gold nanocages may remain elevated. Specifically, a high ratio of payload molecule size to pore size may initially retard the rate of passage of payload molecules through the pores and out of the nanocages following desorption, effectively minimizing initial leaching of desorbed payload molecules out of the local environment of the gold nanocages' hollow interior and maintaining elevated concentration therein. When conditions favorable to electrostatic readsorption are subsequently recreated, the payload molecules that remained within the gold nanocages' hollow interiors may again adsorb onto the interior surfaces thereof. Comparable substantial readsorption onto the external surfaces of the nanocages would not also occur, because the payload molecules desorbed therefrom would have dissipated within the incubation solution and not been maintained in a concentration proximal to the external surfaces' microenvironment sufficiently elevated to permit significant readsorption.

Factors such as the size of nanocages and of their hollow interiors, pore size and morphology relative to size of payload molecules, and valence and magnitude of ligands' and payload molecules' charges, can all be modified in accordance with the present invention. For example, silver nanocubes from which gold nanocages are synthesized can be made of varying sizes to yield gold nanocages of different sizes, according to methods known to skilled artisans. For example, the size of silver nanocubes may be modified by altering the duration of their synthesis, whereby longer durations of synthesis yield more nanocrystal growth and, thus, larger silver nanocubes. Using larger silver nanocubes as templates in a galvanization reaction, in turn, yields larger gold nanocages. Parameters of the galvanic replacement reaction (such as reaction duration, temperature, and concentration of chloroauric acid to silver nanocube) can also be modified according to known protocols to vary the final interior hollow volume of gold nanocages as well as the size and length of pores. The foregoing modifications would be within the knowledge of skilled artisans to obtain gold nanocages possessing preferred morphological characteristics.

Charged ligands may be covalently attached to the surfaces of gold nanocages by a ligand exchange process by which the capping agent used during gold nanocage synthesis (for example, polyvinylpyrrolidone) attached to gold nanocages' surfaces is removed and replaced with charged ligand molecules. Nonexhaustive examples of ligands with a negative charge at neutral pH that could be employed as charged ligands for electrostatically adsorbing positively charged payload molecules include mercaptohexanoic acid, para-mercaptobenzoic acid, mercaptohexadecanoic acid, and 11-mercaptoundecanoic acid. Nonexhaustive examples of ligands with a positive charge at neutral pH that could be employed as charged ligands for electrostatically adsorbing negatively charged payload molecules include aminoethanethiol, N,N,N-trimethyl(11-mercaptoundecyl)ammonium chloride, and cysteamine. Other charged ligands may also be used in accordance with the invention instead of the foregoing. A charged ligand may be a zwitterion, having an overall neutral charge but with localized regions of the molecule containing charge, permitting electrostatic adsorption of payload molecules onto charged ligands. Performing ligand exchange to exchange capping agent molecules for charged ligands leads to covalent bonding of such charged ligands to internal and external surfaces, creating charged surfaces to which payload molecules can adsorb.

When nanocages are subsequently incubated with oppositely charged payload molecules, payload molecules adsorb onto external surfaces but also pass through the gold nanocages' pores, entering their hollow interiors and adsorbing onto internal surfaces. A charged payload molecule may be a zwitterion, having an overall neutral charge but with localized regions of the molecule containing charge, permitting electrostatic adsorption of payload molecules onto charged ligands. Charged payload molecules that may be adsorbed onto gold nanocages in this way include peptides, nucleotides, phospholipids, or synthetic small molecules. The amount of payload molecules that ultimately becomes adsorbed onto interior surfaces is dependent on several factors including the size of the payload molecule, the size of the pores in the gold nanocages, the relative concentrations of gold nanocages and payload molecules incubated together, and the duration of incubation. Narrower and longer pores slow the diffusion of payload molecules into the gold nanocages' hollow interiors and, thus, the accumulation of payload molecules within the hollow interiors and adsorption onto interior surfaces. This is less so for adsorption onto external surfaces, which are accessible to payload molecules without their first having to diffuse through crowded pores. Elevated concentrations of payload molecules and longer incubation durations can also increase the amount of payload molecules adsorbed onto internal surfaces. A sufficiently high concentration of payload molecules and duration of incubation may be selected to achieve saturated adsorption onto internal surfaces as well as external surfaces. The former may reach saturation sooner than the latter at a given concentration of payload molecules used in the incubation reaction.

Figure 2A:
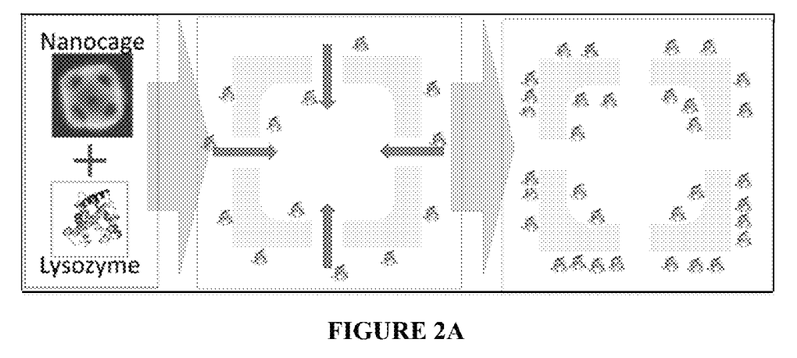
FIGS. 2A-2B are diagrammatic representations of the adsorption, desorption, and readsorption of payload molecules onto surface of gold nanocages.

FIG. 2A is a diagrammatic representation of the process by which payload molecules incubated with gold nanocages containing charged ligands covalently bound to their surfaces results in adsorption of payload molecules onto internal and external surfaces. By way of example, the protein lysozyme is illustrated as one possible payload molecule. Small arrows in the middle panel illustrate the diffusion of payload molecules through the pores of gold nanocages into their hollow interior pores. The right panel shows the accumulated adsorption of payload molecules onto internal and external surfaces of gold nanocages.

In another aspect, it may be desirable to remove payload molecules from the external surfaces of gold nanocages. For example, payload molecules on gold nanocages' external surfaces may undesirably cause agglomeration of gold nanocages, or may undesirably interact with unintended substrates such as extracellular or intracellular membranes, bone, implants, or surfaces of drug delivery systems. To create gold nanocages with payload molecules adsorbed onto the internal surfaces but lacking from external surfaces, temporary desorption can be induced, dissociating payload molecules from external surfaces, which become dispersed in solvent, and from internal surfaces, which are released into gold nanocages' hollow interiors. For example, the ionic strength of the solution can be increased or the pH altered to disrupt the electrostatic attraction between payload molecules and ligands, both internal and external. Much as pore size restricts entry of payload molecules into the interior of gold nanocages before adsorption thereto, so too does it restrict release of payload molecules from gold nanocages' hollow interior. Thus, unlike externally, the concentration of payload molecules in the microenvironment surrounding internal surfaces remains elevated following desorption, at least initially. By returning the ionic strength and/or pH of the solution to conditions that initially favored adsorption while the concentration of desorbed payload molecules remains elevated in the gold nanocages' hollow interior, payload molecules can be readsorbed back onto the interior surfaces. And, because the payload molecules that were desorbed from the external surfaces dissipate in solution, their low local concentration in the microenvironment of the external surfaces would not support substantial readsorption onto external surfaces. The resulting gold nanocages would have payload molecules electrostatically adsorbed onto internal surfaces but not substantially onto external surfaces.

Here, substantially means that the quantity of payload molecules adsorbed onto a nanocage's external surface area is 5% or less of the quantity of payload molecules that would constitute a monolayer thereof adsorbed onto the entire surface area of such nanocage's external surface. The percentage of surface area of nanocages' external surface to which a monolayer of payload molecules is adsorbed after application of a sequence of a desorption step followed by a readsorption step in accordance with the invention disclosed herein may be determined in accordance with the methods disclosed herein and those generally known to skilled artisans. For example, gold nanocages saturated with a monolayer of payload molecules may be subjected to a sequence of a desorption step followed by a readsorption step, using desired conditions in accordance with the current invention and as disclosed herein. Gold nanocubes with the same species of charged ligands attached to their surfaces, and saturated with a monolayer of the same species of payload molecules, as used with the gold nanocages may also be subjected to the same sequence of desorption and readsorption. Gold nanocubes possess only external surface area because they lack pores and hollow interiors. Measuring the fraction of payload molecules desorbed from and not readsorbed onto such gold nanocubes following exposure to such sequence would also therefore indicate the fraction of payload molecules lost from external surfaces of gold nanocages that had also been exposed to the same sequence of desorption and readsorption. If such fraction were 95% or more, then there would not be substantial adsorption of payload molecules to the external surfaces of gold nanocages subjected to such sequence.

Figure 2B:
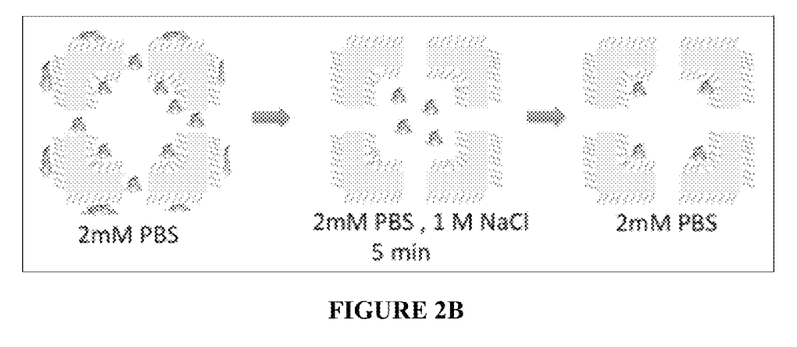

FIG. 2B is a diagrammatic representation of the adsorption, desorption, and readsorption of payload molecules onto the surfaces of gold nanocages. In the left panel, in 2 mM phosphate buffered saline (PBS) that contains 27 mM NaCl, electrostatic interactions between charged payload molecules and charged ligands at physiological pH (7.4) leads to adsorption of payload molecules onto internal and external surfaces of gold nanocages. When subsequently incubated for 5 min in a high ionic strength buffer (in PBS with 1 M NaCl, middle panel), the electrostatic attraction between payload molecules and charged ligand molecules is disturbed and payload molecules are desorbed from gold nanocage surfaces. Externally, payload molecules dissipate within the solution whereas in the hollow core, the concentration of desorbed payload molecules remains high initially due to slow diffusion back out through the gold nanocage's pores. When low ionic strength is returned (2 mM PBS with 27 mM NaCl, right panel), desorbed payload molecules that had been retained in the gold nanocage's hollow core readsorb back onto internal surfaces. Payload molecules that desorbed from the gold nanocage's external surfaces and dissipated in solution, however, do not substantially readsorb onto external surfaces, by comparison.

In another aspect, a gold nanocage may possess payload molecules adsorbed onto its internal surfaces that differ from those adsorbed onto its external surfaces. After payload molecules have been desorbed from internal and external surfaces and readsorbed onto internal surfaces, a different payload molecule could be adsorbed onto external surfaces. This may be desirable, e.g., for targeting gold nanocages to specific cell or tissue types, or promoting or otherwise controlling gold nanocages' internalization by cells and subsequent trafficking within cells. By adsorbing one type of payload molecule for delivery onto internal surfaces and another payload molecule capable of directing targeting or trafficking, for example, of the gold nanocages onto their external surfaces, preferential targeting that is independent of the internally adsorbed payload molecules may be obtained. Adsorbing a payload molecule to external surfaces that differs from those adsorbed to interior surfaces can be obtained by incubating gold nanocages with a different charged payload molecule after readsorption of payload molecules to internal surfaces, when payload molecules have been stripped from external surfaces. If the second payload molecule is too large to fit through the pores of the nanocages, has a lower electrostatic affinity than readsorbed payload molecules for the charged ligands such that it could not displace them from internal surfaces, and/or incubation with the second payload molecules were of a sufficiently short duration to minimize or preclude diffusion of the second payload molecule through nanocages' pores and into the gold nanocages' hollow interior, adsorption of second payload molecules would be largely restricted to external surfaces, resulting in gold nanocages with one payload molecule adsorbed onto its internal surfaces and another payload molecule adsorbed onto its external surfaces. More than one species of payload molecule also may simultaneously be adsorbed onto internal and/or external surfaces, such as by incubating nanocages with a mixture of payload molecules. Or, more than one species of payload molecule may be sequentially adsorbed onto internal and/or external surfaces.

Depending on the species of payload molecule and of charged ligand employed, and their relative charges at different pH levels, release of payload molecules from gold nanocages may preferentially occur in predetermined physiological environments. For example, payload molecules can be adsorbed onto internal surfaces at low NaCl concentrations, or in the absence of NaCl or other salts. Subsequent exposure to physiological concentrations of salt (e.g., approximately 154 mM NaCl) may disrupt the electrostatic attraction between payload molecules and ligand molecules, leading to desorption of payload molecules and their release from gold nanocages at physiological conditions. As an example, if lysozyme were used as a payload molecule and 11-mercaptoundecanoic acid were used as a charged ligand, exposure to physiological concentrations of salt would stimulate desorption of up to 50% or more payload molecules at physiological pH, compared to adsorption levels at lower ionic strengths, and subsequent release from gold nanocages. Skilled artisans would recognize that electrostatic interactions between payload molecules or charged ligand molecules other than the examples described herein could also be disrupted to promote payload molecule release at physiological or other desired ionic strengths, and could determine parameters for making nanocages with internally adsorbed payload molecules that would undergo desorption and leaching at such conditions without excessive or undue experimentation according to well-known methods, including those described herein.

In another aspect, also depending on the characteristics of payload molecules and ligand molecules, payload can be adsorbed onto internal surfaces at one pH at which the charges of charged ligands and payload molecules are of opposite valence and then desorbed upon exposure to a different pH at which the valence of charged ligand and/or payload molecules change such that they are no longer electrostatically attracted to each other, causing release of payload molecules from nanocages. In this sense, the terms "charged ligand" and the "charge" of a payload molecule as discussed herein refer to a ligand and payload molecule bearing electrostatic charges with opposite valence from each other at the pH at which a gold nanocage to which a charged ligand is bound is incubated with payload molecule to promote adsorption, even though the difference between the charged ligand and payload molecule's electrostatic charge may decrease or be eliminated at a different pH, such as to promote desorption and/or payload molecule release. As an example, if lysozyme were used as a payload molecule and 11-mercaptoundecanoic acid were used as a charged ligand, exposure to pH at or above lysozyme's isoelectric point (pH of 11) or at or below 11-mercaptoundecanoic acid's logarithmic acid dissociation constant (pH of 5) may reduce or eliminate the charge differential between payload and ligand, resulting in desorption and release of payload molecules. For example, exposure of such a complex to the environment inside lysosomes, with a pH of 5, would cause loss of charge of 11-mercaptoundecanoic acid, desorption of lysozyme payload, and release thereof from the nanocages. Characteristics of other charged ligands and payload molecules, and the modified pH levels of other environments such as in the gastrointestinal tract, necrotic plaques, or the extracellular environment of tumors, could be similarly exploited to induce release of payload molecules from nanocages at predetermined environments. Skilled artisans would recognize that electrostatic interactions between payload molecules or charged ligand molecules other than the examples described herein could also be disrupted to promote payload molecule release at physiological or other desired pH, and could determine parameters for making nanocages with internally adsorbed payload molecules that would undergo desorption and leaching at such conditions without excessive or undue experimentation according to well-known methods, including those described herein.

Where nanocages may accumulate, such as in tumors as a result of the enhanced permeability and retention effect, or in other environments or cells to which their accumulation has been determined by employing particular externally adsorbed molecules or ligands, a slow, long term release of payload molecules from nanocages may beneficially cause a sustained, steady-state level of exposure of tissue to payload molecules compared to what can be obtained with traditional methods for administering therapeutics or other molecules of interest.

Relationships between diffusion kinetics, pore size, and payload molecule size can be altered to modify the amounts of payload molecules adsorbed internally to gold nanocages. Two parameters may determine leaching of desorbed payload molecules from gold nanocages: diffusion of payload molecules from the hollow interior into a pore (core-pore diffusion), and payload molecules migration though the pore to be released to the surrounding solution (through-pore diffusion). Core-pore diffusion is determined by the difference between the concentration of payload molecules in a pore and in the hollow core of the gold nanocage:

$$J_{core\text{-}pore} = \begin{cases} D_0 \dfrac{C_{core} - C_{pore}}{\frac{d}{2}}, & t = 0 \\ D_0 \dfrac{C_{core} - C_{solution}}{\frac{d}{2}}, & t > 0 \end{cases}, \quad (1)$$

d denotes diameter of the nanocage internal hollow core, $J_{core-pore}$ denotes the payload molecule flux into pores, $C_{core}$ denotes the payload molecule concentration inside hollow cores, $C_{pore}$ denotes the payload molecule concentration inside pores, $C_{solution}$ denotes the free payload molecule concentration outside the gold nanocages, and $D_0$ is the free payload molecule diffusivity in bulk solution, as calculated by the Einstein-Stokes equation.

Similarly, the through-pore diffusion is described by Eq 2:

$$J_{thru-pore} = \begin{cases} D\dfrac{C_{pore} - C_{solution}}{l}, t = 0 \\ D\dfrac{C_{core} - C_{solution}}{l}, t > 0 \end{cases} \quad (2)$$

l denotes the nanocage pore length, $J_{thru-pore}$ denotes the payload molecule flux through pores, and D denotes the through-pore diffusivity calculated by the Higdon-Muldowney equation (Eq 3), where λ is the effective diffusant-pore ratio:

$$\dfrac{D}{D_0} = 1 + \dfrac{9}{8}\lambda \ln \lambda - 1.5603\lambda + 0.528155\lambda^2 + 1.91521\lambda^3 - \quad (3)$$
$$2.81903\lambda^4 + 0.270788\lambda^5 + 1.10115\lambda^6 - 0.435933\lambda^7$$

As a quantified hypothetical approximation, in one example, the dimension of the hollow core may be an approximate cube that is 50 nm×50 nm×50 nm at each of its edges; the dimensions of the cylindrical pore may be 5 nm in radius and 10 nm in length, and the dimension of a hypothetical payload molecule may be, for example, 1.5 nm in radius (as measured by calculating the molecule's gyration radius). Gyration radius may be determined from a payload molecule's crystal structure, such as determined by X-ray crystallography by known methods. For a hypothetical example, $C_{core}$ immediately upon desorption could be estimated to be in the millimolar range (e.g., 20 mM) when $C_{solution}$ could be estimated to be in the micromolar range (e.g., 20 μM), both approximated as constant during payload leaching.

Because pore surfaces may also be covered by payload molecules, a critical hypothetical boundary condition reflecting the crowding of pores at the beginning of leaching and consequent, significant hindrance of through-pore diffusion can be estimated. Quantitatively, the number of payload molecules with hypothetical gyration radius of 1.5 nm inside each pore may be about 5~10 (equilibrated with the hollow core), and due to the small pore volume and crowded pore environment, these molecules can be approximately treated as one large diffusant molecule, making an effective diffusant-pore ratio (λ) about 0.9, rendering D≈$10^{-4}$ $D_0$ according to Eq (3). Using this D value, as well as all the approximate quantities above, Eqs. 1 and 2 yield that $J_{core-pore} \gg J_{thru-pore}$ at t=0, indicating not only that the through-pore diffusion is rate-determining at the beginning of the leaching process, but that the pore would remain filled up by payload molecules until $C_{core}$ is at near equilibrium with $C_{solution}$. Therefore, λ remains at around 0.9 and D remains magnitudes lower than $D_0$ during most of the leaching process. From these estimates, it is apparent that even if all the internal and external payload molecules were completely desorbed immediately upon exposure to high ionic strength buffer, a hypothetical potentiality that may be unlikely to occur, particularly for payload molecules adsorbed to internal surfaces, after 10 min of leaching, ~30% of the internal payload molecules would still remain inside gold nanocages.

Depending on payload molecule size and pore diameter and length, therefore, profiles of payload leaching during desorption can be modified to attain desired levels of payload molecules that remain within the hollow nanocages' core to permit their readsorption. Parameters employed during galvanic replacement-formation of gold nanocages, including the relative concentrations of chloroauric acid and silver nanocubes, duration of galvanic replacement, and temperature profiles, including duration of elevated temperature before, during, and after galvanic replacement, can be modified to create gold nanocages of varying pore dimensions, which modifications would be easily apprehended and adopted by skilled practitioners in the field. For gold nanocages with pores whose radius is within 1-5 times a gyration radius of payload molecules and whose length is 20 nm or less, leaching of payload molecules during desorption may be sufficiently curtailed to permit desorption of payload molecules from external surfaces of gold nanocages without readsorption while permitting significant readsorption onto internal surfaces. Pores with radii that are at least 1.2-times or up to 20-times a gyration radius of payload molecules may have adsorption and/or leaching profiles that are particularly advantageous in certain circumstances in accordance with the current invention.

Gold nanocages used in this way as carriers for various payload molecules have significant applicability as delivery agents for therapeutic agents or as tools for research. The biocompatibility and low toxicity of gold nanocages is known, rendering them suitable for administration to patients for delivery of payload molecules systemically or localized to particular tissues. Furthermore, payload molecules adsorbed to interior nanocage surfaces retain biological functionality. Thus, disorders typified by absence or low levels, or malfunctioning of identified endogenous peptides or other biomolecules could be remedied by delivering gold nanocages containing payload molecules that restore or augment functionality to such individuals with such disorders. Gold nanocages carrying remedial payload molecules may be injected into a patient in need of treatment, intravenously, intracerebroventricularly, intraperitoneally, or directly into an organ of interest. Test reagents or biomolecular tools as payload molecules in gold nanocages may also be delivered to tissue, cell, or in vitro samples in research settings, where prolonged and controlled delivery of reagents is desired.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

EXAMPLES

Aspects of the present invention now will be further illustrated by, but by no means are limited to, the following Examples Silver nanocubes and gold nanocages were synthesized based on the galvanic replacement method known to skilled artisans and as reported by Skrabalak et al. (*Nat. Protoc.* 2007, 2, 2182-2190). Silver nanocube templates were synthesized via the reduction of $AgNO_3$ in heated ethylene glycol (0.5 ml at a concentration of 0.048 g/ml), while using polyvinylpyrrolidone (PVP) in ethylene glycol (1.5 ml at a concentration of 0.02 g/ml) and Na$_2$S in ethylene glycol (0.06-0.1 ml at a concentration of 3 mM) to control reaction rate and product morphology. The concentration of Na$_2$S and reaction times were carefully controlled to ensure a good yield of distinct silver nanocube templates with uniform structure. For example, 0.06-0.07 ml of Na$_2$S in ethylene glycol may be used. Subsequently, silver nanocube substrates in suspension were used as sacrificial templates in the galvanization reaction (eq 4) to obtain gold nanocubes.

$$3Ag(s) + AuCl_4^-(aq) \rightarrow Au(s) + 3Ag^+(aq) + 4Cl(aq) \quad (4)$$

In the galvanization reaction, aqueous HAuCl$_4$ solution was added to a boiled aqueous silver nanocube solution with a syringe pump. The concentration of silver nanocubes was about 0.02 mg/ml (i.e., 2 nM in terms of nanoparticle quantity), the concentration of HAuCl$_4$ was 0.1 mM, and the volume ratio between silver nanocube suspension and HAuCl$_4$ solution was from 10:1 to 2:1 (the lower the Ag:Au ratio, the larger the nanocage pore). Feeding rate of HAuCl$_4$ was around 0.75 ml/min. A dramatic color change from pale yellow to grayish blue was observed during galvanization. The reaction was heated to 100 degrees C. from 5 minutes before until 5 minutes after addition of HAuCl$_4$. The polyol synthesis of gold nanocubes followed the protocol known to skilled artisans and reported by Seo et al. (*J. Am. Chem. Soc.* 2006, 128, 14863-14870). Briefly, HAuCl$_4$ and PVP were added into heated 1,5-pentanediol with refluxing and AgNO$_3$ was added. A variety of characterization methods, including scanning electron microscopy and x-ray diffraction, were used to determine the morphology and uniformity of the nanoparticles. After their morphologies had been confirmed, the nanoparticles underwent a ligand exchange process. The ligand exchange and subsequent characterizations followed a protocol known to skilled artisans and previously reported by Gagner et al. (*Biomaterials* 2012, 33, 8503-8516). Specifically, gold nanoparticles were incubated in ethanol with 10 mg/ml 11-mercaptoundecanoic acid (11-MUA) to replace the nanoparticle surface ligand from PVP to 11-MUA. After the ligand exchange, gold nanocages were stored in 2 mM PBS with 27 mM NaCl (pH 7.4) and were ready for subsequent protein experiments.

Skilled artisans would recognize that nanocages may also be formed by other well-known methods, in accordance with the present invention. For example, nanocages may be formed by core-shell synthesis, wherein a layer of gold: silver alloy is grown outside a nanoparticle template, then the template is removed such as by etching, sintering, dissolving, etc., leaving a nonparticle with pores and a hollow core (i.e., a nanocage). Additional galvanization methods may also be employed, according to methods well-known to skilled artisans, within the scope of the present invention. For example, a silver nanoparticle may be galvanized with platinum to form a platinum nanocage. Silica nanocages may also be synthesized via a sol-gel method, which may be grafted by charged ligands.

In an example, the protein lysozyme (Lyz) was used as a payload molecule. In addition to adsorbing Lyz onto gold nanocages, for comparative purposes gold nanocubes were also synthesized for adsorption of Lyz onto their external surfaces. Gold nanocubes are similar to gold nanocages in size, composition, and dimensions, except that gold nanocubes lack the pores and hollow cores of gold nanocages. Therefore, unlike gold nanocages, gold nanocubes can only have payload molecules adsorbed onto their external surfaces, as they lack internal surfaces. By comparing the characteristics of gold nanocages with Lyz adsorbed to that of gold nanocubes with Lyz adsorbed, the presence and effects of Lyz adsorbed onto internal surfaces can be distinguished from those of its adsorption onto external surfaces. Gold nanocubes were synthesized according to published methods previously known to skilled artisans, such as disclosed by Gagner et al. (*Biomaterials* 2012, 33, 8503-8516). HAuCl$_4$ and PVP were added into heated 1,5-pentanediol with refluxing, and AgNO$_3$ was carefully added to control gold nanocube morphology.

Approximately 100 µg/ml Lyz was incubated with approximately 2 nM gold nanocages or gold nanocubes in PBS buffer (2 mM, 27 mM NaCl, pH=7.4) for 3 days to ensure thorough protein internalization. To remove externally bound proteins, both gold nanocage-Lyz and gold nanocube-Lyz nanobioconjugates were subjected to a high-salt buffer to screen the electrostatic attractions between nanoparticles and proteins. Briefly, 800 µL of nanobioconjuates in PBS buffer with 27 mM NaCl were mixed with 200 µl 5 M NaCl aqueous solution. The mixed solutions were then shaken for 5 min to balance the thorough removal of external Lyz and the best preservation of internal Lyz. After shaking, nanobioconjuagates were gently centrifuged at 5000 rpm for 3 min twice to remove any unbound proteins, and finally re-dispersed in 500 µL 2 mM PBS buffer with 27 mM NaCl (pH 7.4). The centrifuged supernatants were subjected to µBCA (microbicinchoninic acid) and bicinchoninic acid (BCA) assays to measure their protein concentrations, and the protein amount remaining on gold nanocages or gold nanocubes was calculated by subtracting the protein amount in the supernatant from the total added protein amount. A control group of nanobioconjugates treated with deionized water instead of NaCl solution was used for each nanobioconjugate titration to determine the amount of adsorbed proteins before NaCl wash.

The enzymatic activity of gold nanocage-Lyz and gold nanocube-Lyz conjugates was measured in a fluorescence assay by measuring the fluorescent intensity of 7-hydroxy-4-methylcoumarin (4-MU) that was cleaved from Lyz-catalyzed hydrolysis of 4-MU-β-(GluNAc)$_3$. Washed gold nanocage-Lyz and gold nanocube-Lyz conjugates were centrifuged to remove free Lyz and incubated at 37° C. with 2 ml of 0.09 mg/ml 4-MU-β-(GluNAc)$_3$ prepared in sodium phosphate buffer (0.1 M, pH 6.5). During incubation, 300 µl aliquots were taken at 0, 2, 4, 8 and 20 h, respectively, and immediately mixed with the same amount of glycerin buffer (0.8 M, pH 10.4) to quench the reaction. The mixed aliquots were then centrifuged again to remove the nanoparticles, which could potentially interfere with the fluorescence measurement. After centrifugation, supernatants that contain 4-MU residue were transferred to a 96-well plate, and the concentration of 4-MU was measured in triplicate using fluorescence spectroscopy ($\lambda_{ex}$=355 nm, $\lambda_{em}$=460 nm). A free Lyz solution sample was also involved in this assay as a control. The specific activity of each nanobioconjugate sample was normalized with respect to the same concentration of free Lyz.

The enzymatic activity of gold nanocage-Lyz and gold nanocube-Lyz conjugates was also measured in the cell wall assay, with *Micrococcus lysodeikticus* as the substrate. Turbidity measurements of *M. lysodeikticus* were monitored at 450 nm for 300 s. *M. lysodeikticus* solution was prepared in 30 mM potassium phosphate buffer (pH 7.4) and diluted to an absorbance of 0.6 AU. Then 100 µL of washed gold nanocube-Lyz or gold nanocage-Lyz conjugate was added to 900 µl of *M. lysodeikticus* solution. Incubation of *M. lysodeikticus* with active Lyz results in decreased solution turbidity as the cells are lysed. Specific activity was normalized against the activity of the same concentration of free Lyz.

As shown in Table 1, after 5 min of 1 M NaCl incubation, little Lyz remained on the surfaces of gold nanocubes, whereas ~45% Lyz adsorbed onto gold nanocages was retained in the nanobioconjugates. Most of the remaining Lyz in the gold nanocage nanobioconjugates was therefore readsorbed at the internal surface after being desorbed in low salt buffer.

TABLE 1

Amount of adsorbed Lyz before and after NaCl wash

| | Nanoparticle concentration (nM) | Adsorbed Lyz before salt wash (μg/ml) | Adsorbed Lyz after salt wash (μg/ml) | Estimated surface coverage |
|---|---|---|---|---|
| AuNC | 0.12 | 7.3 ± 0.5 | 0.1 ± 0.1 | 2% |
| AuNG | 0.46 | 25.0 ± 3.0 | 12.0 ± 3.0 | 0~10% external; 100~120% internal |

Figure 3A:
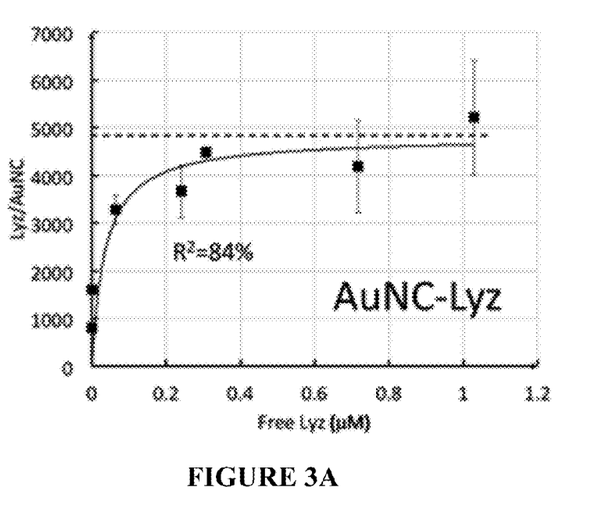
FIGS. 3A-3B are Langmuir adsorption isotherms showing saturation levels of a payload molecule lysozyme adsorbed onto gold nanocubes and gold nanocages.
Figure 3B:
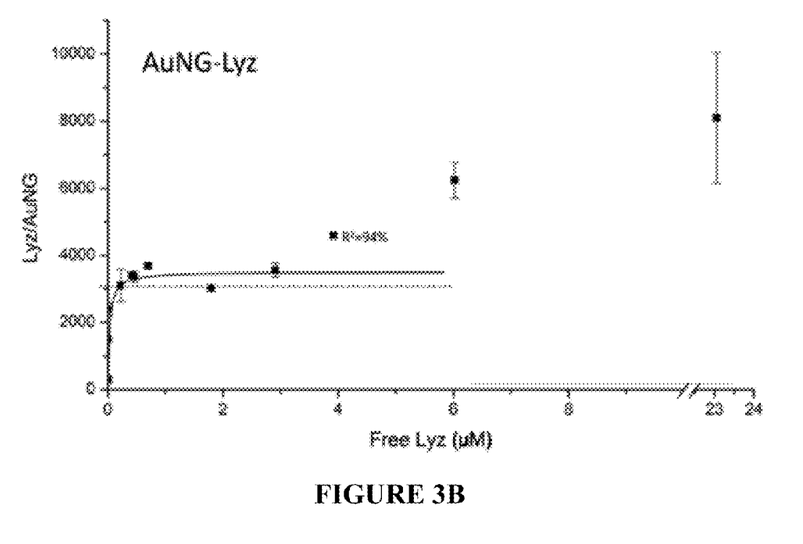

Protein adsorption was quantified using the microbicinchoninic acid (μBCA) and bicinchoninic acid (BCA) assays to determine the amount of protein in solution after two rounds of centrifugation. Adsorption curves were fitted to the classical Langmuir isotherm to determine the number of binding sites on the nanoparticles, as well as the apparent dissociation constants for each conjugate. The data points and fitted adsorption pseudoisotherms are shown in FIGS. 3A (for gold nanocubes) and 3B (for gold nanocages). The protein uptake curve of gold nanocages shows two distinct regions, as is commonly observed for mesoporous silica when proteins adsorb to both exterior and interior surfaces, first saturating at low concentrations ([free Lyz]<1 μM), then dramatically increasing at [free Lyz]=2-3 μM, and finally approaching saturation at higher free protein concentrations ([free Lyz]>10 μM). The first region ([free Lyz]<3 μM) of the gold nanocage-Lyz uptake curve can be fitted by a Langmuir isotherm, resulting in Lyz uptake of 3500±400 molecules/gold nanocage. For comparison, the Langmuir fit for gold nanocube-Lyz conjugates (FIG. 3A) estimates a Lyz uptake of 4800±500 molecules/gold nanocube.

After 5 min incubation in a high-salt buffer (1 M NaCl, 2 mM PBS), gold nanocages still had about a half of the Lyz adsorbed and functional, whereas a solid, non-hollow gold nanocube loses almost all of its adsorbed proteins under the same conditions. This demonstrated that the NaCl-wash can remove the externally adsorbed proteins on either gold nanocages or gold nanocubes, due to the screening effect, but the majority of internally adsorbed proteins in gold nanocages are temporarily restrained by the nanocage walls, permitting readsorption to internal surfaces.

Figure 4A:
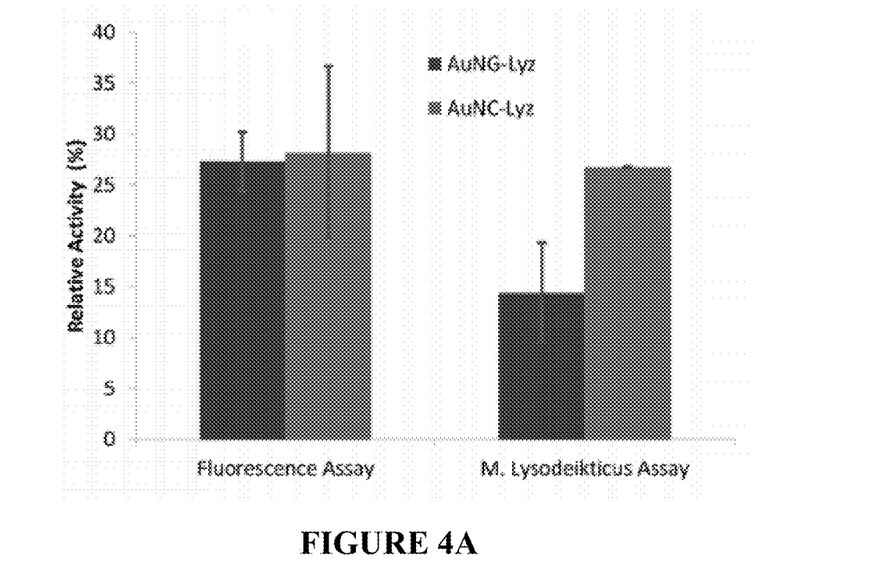
FIG. 4A shows enzymatic activity of a payload molecule lysozyme adsorbed onto gold nanocubes and gold nanocages as measured in different assays.
Figure 4B:
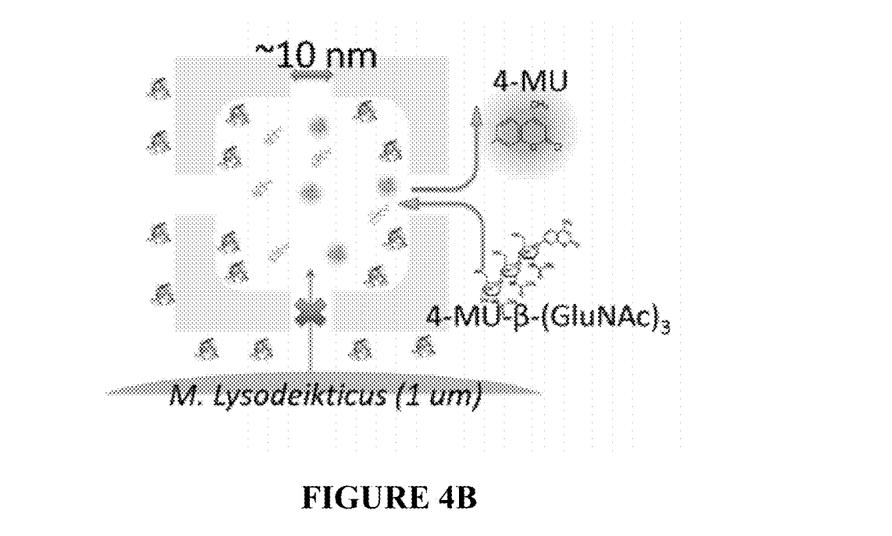
FIG. 4B is a diagrammatic representation of different enzymatic assays for a payload molecule lysozyme.

The enzymatic activities of nanocube-Lyz and nanocage-Lyz nanobioconjugates were measured in two assays as described above. FIG. 4A is a graph showing the results of these assays. Relative activity, on the Y-axis, represents enzymatic activity relative to free Lyz. The bars on the left show the relative activity of the nanobioconjugates in the fluorescence activity, and the bars on the right show the relative activity of the nanobioconjugates in the cell wall assay. Results for gold nanocage-Lyz are shown in dark gray and results for gold nanocube-Lyz are shown in light gray. Compared with free Lyz, the gold nanocube-Lyz retained ~28% of their native activity in both assays. Interestingly, for gold nanocage-Lyz nanobioconjugates, the fluorogenic substrate activity, versus free enzyme, resulted in a nearly identical activity as that with gold nanocubes, yet indicated only ca. 15% of native activity in the cell wall assay, a reduction owing to the inaccessibility of Lyz conjugates on internal surfaces to the substrate in this assay, as shown in FIG. 4B.

Figure 5:
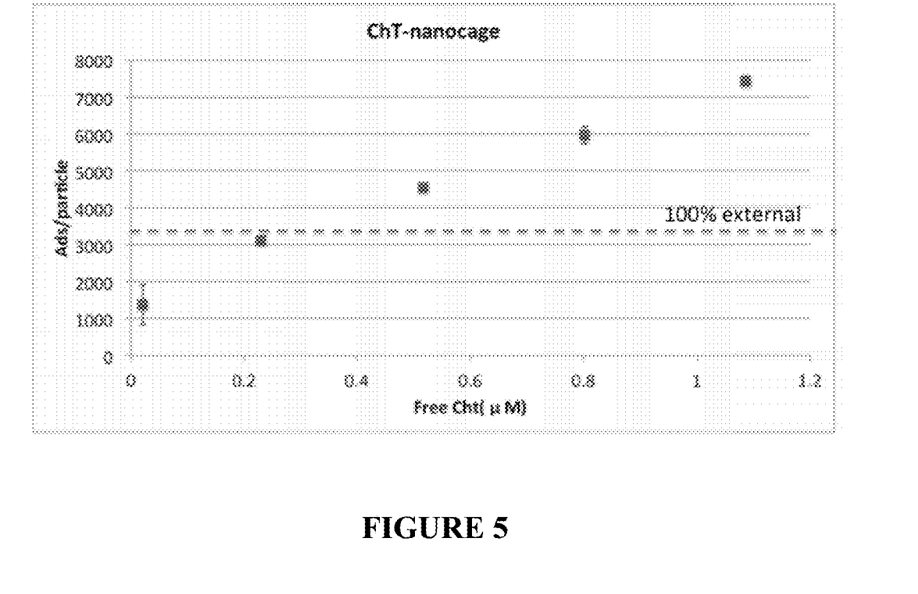
FIG. 5 is a graph of adsorption saturation of gold nanocages with a payload molecule chymotrypsin.

In another example, α-chymotrypsin (ChT) was used as the payload molecule instead of Lyz. The data points and fitted adsorption pseudoisotherm for adsorbing ChT onto gold nanocages is shown in FIG. 5. The dotted line indicates the saturation amount of protein loading that would be predicted if there were only adsorption onto external surfaces. The continued protein adsorption to nanocages above this level with increasing concentrations of ChT incubation signifies adsorption onto internal surfaces in addition to external surfaces.

While several aspects of the present invention have been described and depicted herein, alternative aspects may be effected by those skilled in the art to accomplish the same objectives. Accordingly, it is intended by the appended claims to cover all such alternative aspects as fall within the true spirit and scope of the invention.

The invention claimed is:

1. A nanoparticle comprising:
   a gold nanocage comprising pores;
   charged ligand molecules covalently bound to one or more surfaces of the gold nanocage, wherein at least some charged ligand molecules are covalently bound to internal surfaces of the gold nanocage; and
   payload molecules electrostatically adsorbed onto said charged ligand molecules covalently bound to internal surfaces of the gold nanocage, wherein a diameter of one or more pores in the gold nanocage is between 1.2 and 20 times a gyration radius of the payload molecule.

2. The nanoparticle of claim 1, wherein charged ligand molecules are covalently bound to an external surface of the gold nanocage and payload molecules are electrostatically adsorbed onto said charged ligand molecules covalently bound to external surfaces of the gold nanocage.

3. The nanoparticle of claim 1, wherein the charged ligand molecules are negatively charged at physiological pH.

4. The nanoparticle of claim 1, wherein charged ligand molecules are positively charged at physiological pH.

5. The nanoparticle of claim 1, wherein payload molecules comprise nucleic acids, polypeptides, enzymes, antibodies, phospholipids, or any combination of the foregoing.

6. The nanoparticle of claim 1, wherein payload molecules are not electrostatically adsorbed onto charged ligand molecules covalently bound to external surfaces of the gold nanocage.

7. The nanoparticle of claim 1, wherein a radius of pores in the gold nanocage is between 1.2 and 5 times a gyration radius of the payload molecule and a length of the pores is between 1 nm and 20 nm.

8. The nanoparticle of claim 3, wherein payload molecules comprise nucleic acids, polypeptides, enzymes, antibodies, phospholipids, or any combination of the foregoing.

9. The nanoparticle of claim 4, wherein payload molecules comprise nucleic acids, polypeptides, enzymes, antibodies, phospholipids, or any combination of the foregoing.

10. A nanoparticle comprising:
    a gold nanocage comprising pores;
    charged ligand molecules covalently bound to one or more surfaces of the gold nanocage, wherein at least some charged ligand molecules are covalently bound to internal surfaces of the gold nanocage; and
    payload molecules electrostatically adsorbed onto said charged ligand molecules covalently bound to internal surfaces of the gold nanocage, wherein a diameter of one or more pores in the gold nanocage is between 1.2 and 20 times a gyration radius of the payload molecule;

wherein the charged ligand molecules comprise ligands having a negative charge at physiological pH and the ligands having a negative charge at physiological pH are selected from the group consisting of mercaptohexanoic acid, para-mercaptobenzoic acid, mercaptohexadecanoic acid, and 11-mercaptoundecanoic acid.

11. The nanoparticle of claim 10, wherein the ligands having a negative charge at physiological pH are 11-mercaptoundecanoic acid.

12. The nanoparticle of claim 10, wherein charged ligand molecules are covalently bound to an external surface of the gold nanocage and payload molecules are electrostatically adsorbed onto said charged ligand molecules covalently bound to external surfaces of the gold nanocage.

13. The nanoparticle of claim 10, wherein payload molecules comprise nucleic acids, polypeptides, enzymes, antibodies, phospholipids, or any combination of the foregoing.

14. The nanoparticle of claim 11, wherein payload molecules comprise nucleic acids, polypeptides, enzymes, antibodies, phospholipids, or any combination of the foregoing.

15. The nanoparticle of claim 10, wherein payload molecules are not electrostatically adsorbed onto charged ligand molecules covalently bound to external surfaces of the gold nanocage.

16. The nanoparticle of claim 10, wherein a radius of pores in the gold nanocage is between 1.2 and 5 times a gyration radius of the payload molecule and a length of the pores is between 1 nm and 20 nm.

17. A nanoparticle comprising:
a gold nanocage comprising pores;
charged ligand molecules covalently bound to one or more surfaces of the gold nanocage, wherein at least some charged ligand molecules are covalently bound to internal surfaces of the gold nanocage; and
payload molecules electrostatically adsorbed onto said charged ligand molecules covalently bound to internal surfaces of the gold nanocage, wherein a diameter of one or more pores in the gold nanocage is between 1.2 and 20 times a gyration radius of the payload molecule;
wherein the charged ligand molecules comprise ligands having a positive charge at physiological pH and the ligands having a positive charge at physiological pH are selected from the group consisting of aminoethanethiol, N,N,N-trimethyl(11-mercaptoundecyl)ammonium chloride, and cysteamine.

18. The nanoparticle of claim 17, wherein charged ligand molecules are covalently bound to an external surface of the gold nanocage and payload molecules are electrostatically adsorbed onto said charged ligand molecules covalently bound to external surfaces of the gold nanocage.

19. The nanoparticle of claim 17, wherein payload molecules comprise nucleic acids, polypeptides, enzymes, antibodies, phospholipids, or any combination of the foregoing.

20. The nanoparticle of claim 17, wherein payload molecules are not electrostatically adsorbed onto charged ligand molecules covalently bound to external surfaces of the gold nanocage.

21. The nanoparticle of claim 17, wherein a radius of pores in the gold nanocage is between 1.2 and 5 times a gyration radius of the payload molecule and a length of the pores is between 1 nm and 20 nm.

* * * * *